United States Patent
Le

(10) Patent No.: US 6,959,267 B2
(45) Date of Patent: Oct. 25, 2005

(54) METHOD OF INSPECTING A HEAT EXCHANGER AND COMPUTER PROGRAM PRODUCT FOR FACILITATING SAME

(75) Inventor: Qui V. Le, Pittsburgh, PA (US)

(73) Assignee: Westinghouse Electric Co. LLC, Pittsburgh, PA (US)

( * ) Notice: Subject to any disclaimer, the term of this patent is extended or adjusted under 35 U.S.C. 154(b) by 28 days.

(21) Appl. No.: 10/816,146

(22) Filed: Apr. 1, 2004

(65) Prior Publication Data

US 2005/0154564 A1 Jul. 14, 2005

Related U.S. Application Data

(60) Provisional application No. 60/535,297, filed on Jan. 9, 2004.

(51) Int. Cl.[7] ............................................. G06F 19/00
(52) U.S. Cl. ........................................ 702/189; 702/38
(58) Field of Search ................... 165/11.2; 73/514.14, 73/519.01, 865.8; 324/222; 702/33, 34, 35, 702/36, 38, 57, 64, 66, 71, 150, 182, 183, 702/184, 185, 127, 189

(56) References Cited

U.S. PATENT DOCUMENTS

| | | | |
|---|---|---|---|
| 3,302,105 A | 1/1967 | Libby et al. | |
| 3,693,075 A | 9/1972 | Forster | |
| 4,194,149 A | 3/1980 | Holt et al. | |
| 4,207,520 A | 6/1980 | Flora et al. | |
| 4,586,249 A * | 5/1986 | Costlow et al. | 29/723 |
| 4,631,688 A | 12/1986 | Boehm et al. | |
| 4,757,258 A * | 7/1988 | Kelly et al. | 324/220 |
| 4,763,274 A | 8/1988 | Junker et al. | |
| 4,856,337 A * | 8/1989 | Metala et al. | 73/601 |
| 5,321,887 A | 6/1994 | Boula | |
| 5,751,610 A | 5/1998 | Gan et al. | |
| 5,838,882 A | 11/1998 | Gan et al. | |
| 5,878,151 A | 3/1999 | Tang et al. | |
| 6,282,461 B1 | 8/2001 | Gan et al. | |

\* cited by examiner

Primary Examiner—Bryan Bui
Assistant Examiner—Douglas N. Washburn

(57) ABSTRACT

A method of inspecting a heat exchanger including a plurality of tubes having ends fixed in a tubesheet includes the steps of: establishing a baseline for each tube of its location in the tubesheet and its unique eddy current pattern resulting, at least in part, from fixing the tube end in the tubesheet; inserting an eddy current probe into a first identified tube; obtaining eddy current data for the first identified tube in the region of the tubesheet; comparing the eddy current data obtained for the first identified tube with the baseline eddy current data for the tube, in order to verify the correctness of the tube identification; and accepting the obtained eddy current data if the correctness of the tube identification has been verified by the comparison. A computer program product for automatically carrying out the steps of the foregoing method is also disclosed.

20 Claims, 8 Drawing Sheets

FIG. 6

METHOD OF INSPECTING A HEAT EXCHANGER AND COMPUTER PROGRAM PRODUCT FOR FACILITATING SAME

CROSS-REFERENCE TO RELATED APPLICATION

The present application is a traditional application claiming priority to Provisional Application Ser. No. 60/535,297, filed on Jan. 9, 2004, entitled "A Method of Inspecting A Heat Exchanger," which is incorporated herein by reference.

BACKGROUND OF THE INVENTION

1. Field of the Invention

The present invention relates generally to a method of inspecting a heat exchanger and, more particularly, to a method of using unique, tube-specific tubesheet eddy current signal characteristics to verify the identity of individual steam generator tubes having ends disposed in a tubesheet. The invention also relates to a computer program product for performing a method of inspecting steam generator tubes.

2. Background Information

Heat exchangers, such as, for example, steam generators used in pressurized water nuclear powered electric generating systems, generally include thousands of U-shaped heat exchanger tubes disposed within a generally cylindrical pressure vessel. The ends of the heat exchanger tubes are secured within a transverse plate called a tubesheet, which separates the steam generator into a primary side and a secondary side. Heated primary fluid from the nuclear reactor is passed through the tubes to effectuate a heat transfer with the secondary working fluid which, in turn, drives the turbo-machinery used to generate electricity. The primary fluid can be radioactive. Accordingly, to prevent leakage of the reactor coolant into the secondary side of the generator, which would contaminate the steam, the heat transfer tubes must be periodically inspected for flaws and degradation such as cracks, pits, dents and tube wall thinning. If a degraded tube is discovered, it is typically plugged at both ends. In view of the thousands of tubes in the steam generator, plugging of a few tubes does not appreciably affect the efficiency of the heat transfer.

Eddy current testing is a well known, commonly used method of nondestructive testing of steam generator tubes. Generally, in performing an eddy current test on steam generator tubes, a sensor or probe is advanced through the tube as signals are generated and recorded for later analysis. See, e.g., U.S. Pat. No. 3,302,105 (illustrating and describing the eddy current signatures of various types of tube defects); see also U.S. Pat. Nos. 3,693,075; 4,194,149; 4,207,520; and 4,631,688. U.S. Pat. No. 4,763,274, which was filed on Jun. 24, 1986 and issued to the assignee hereof, discloses eddy current inspection processes for nuclear steam generator tubes and computer analysis of the eddy current data for automatically detecting flaws in the heat transfer tubes of a steam generator.

The Electrical Power Research Institute (EPRI) is developing new criteria for data quality acceptance in eddy current steam generator inspection. One such requirement is to verify and ensure that the eddy current sensor or inspection probe is delivered to the correct tube for inspection thereof. Conducting efficient tube inspection and/or repair while minimizing the impact of such inspection on the steam generator operations (i.e., minimizing the downtime required for such inspection), requires quick and accurate tube identification and the ability to record information with respect to each tube for future reference and comparison.

Historically, heat exchanger tube inspection involved the use of technicians who would conduct tests using a variety of inspection devices (i.e., an eddy current probe) and then record the results for future reference. In view of the thousands of tubes in a typical generator, this was an extremely time consuming, arduous and tedious procedure, the results of which were highly susceptible to human error. Ensuring the accurate identity of an individual tube or relocating to a tube was also very difficult. Accuracy was dependent on the analyst correctly counting tubes to locate the desired tube. Moreover, it was a dangerous process, potentially exposing the technicians to an unacceptable dose of radiation.

A relatively recent improvement upon such manual inspections involves the use of computer controlled robotic arms with specialized end-effectors capable of conducting the inspection or repair. Generally, the robotic arm is secured beneath the tubesheet with the end-effector mounted at the end of the arm. The end-effector typically comprises an assembly mounted on the end of the robotic arm and including, for example, a television camera, one or more illumination sources, inspection tools, such as an eddy current sensor or probe, and tooling to plug effected tubes. A computer, under the control of an operator, is used to control the robotic arm. The operator can move the end-effector across the tubesheet using, for example, a joystick or by specifying a target tube destination using x, y cartesian coordinates. U.S. Pat. Nos. 5,751,610, 5,838,882 and 5,878,151, disclose several representative prior art robotic arm end-effectors for use in inspecting steam generator tubes. However, while such robotic systems have improved the inspection process, they are relatively deficient at pinpointing or relocating to a specific tube, in order to, for example, check on the status of the tubes degradation or the integrity of a prior tube repair.

Accordingly, there have been several attempts to improve the accuracy and efficiency with which industrial steam generator tubes are identified. Known prior art methods of tube identification involve, for example, physical modification of the tube ends to create a computer readable marking system or use of a computerized tube position visualization and verification system.

U.S. Pat. No. 5,321,887, for example, discloses a process of marking each tube with a binary bar code formed from circular impressions and the absence of such impressions. The bar code is embossed on the exterior of the tubes during manufacture or alternatively on the interior of the tubes after they have been fixed in the tubesheet. A cartography is then produced in the factory or after installing the steam generator in the nuclear power station, using the bar codes to associate position information, in Cartesian coordinates, with the location of each tube in the tubesheet. When it is subsequently desired to locate a given tube, a computer is used to access the cartography and to provide automated control of the robotic arm to the desired tube. However, such a method requires physical modification of the tubes and is timely and costly to implement, particularly when modifying an existing steam generator to implement the technology.

U.S. Pat. No. 6,282,461, which was filed on Jul. 9, 1999 and issued to the assignee hereof, discloses an independent tube position verification system including a television camera mounted on the robotic arm end-effector, in order to visually track changes in position as the robotic arm changes position with respect to the tubesheet. The camera outputs successive image frames in order to track the physical displacement of a recognizable reference artifact, such as a plugged tube, as the end-effector moves across the tubesheet. The physical displacement information is then converted into velocity and direction information and compared against position information maintained by the robotic arm encoder. Mismatched readings indicate a loss of tracking integrity requiring re-calibration of the system.

Such image capturing and analysis systems are susceptible to several disadvantages. Factors such as illumination and associated shadows, robot arm bending, absence of an adequate reference artifact from which to calculate displacement and camera image distortion caused by, for example, the speed at which the end-effector is traveling and the end-effector's location relative to the tubesheet, can negatively impact the accuracy of the system. Calibration of robotic inspection systems can be problematic. The accuracy of the robotic arm and end-effector movement depends on the robot system design, calibration, the robot's onboard encoder or analyzer and communication of the robot with the computer control system. For example, it is not uncommon for the robotic arm to be subject to bending forces, particularly when it is fully extended with respect to its mounting location. Such bending can result in the robotic arm being located at a distance and location different from that calculated by the robot's onboard tube locating encoder or analyzer. It is, therefore, possible for the wrong tube to be inspected and/or repaired, thereby resulting in the potential of plugging or repairing a perfectly good tube or leaving a degraded tube un-inspected or un-repaired and returning it to service in its degraded condition. Additionally, known prior art methods of tube identification, whether from the robot or from the tube position verification system, do not update the data collection system to include the current status of the tube for updated future reference.

There is a need, therefore, for a method of quickly and accurately identifying and verifying the identity of the tubes of a steam generator for inspection and/or service thereof, that overcomes the aforementioned disadvantages.

Accordingly, there is room for improvement in heat exchanger inspection and in heat exchanger tube identification and verification.

SUMMARY OF THE INVENTION

These needs and others are satisfied by the present invention, which provides a fast and accurate process of identifying and verifying the identity of individual tubes in a heat exchanger, such as the steam generator of a nuclear power generation station.

As one aspect of the invention, a method of inspecting a heat exchanger comprising a plurality of tubes having ends fixed in a tubesheet comprises the steps of: establishing a baseline for each tube of its location in the tubesheet and its unique signal pattern resulting, at least in part, from fixing the tube end in the tubesheet; obtaining signal pattern data at an elevation proximate a first identified tube; comparing the signal pattern data obtained for the first identified tube with the baseline signal pattern, resulting at least in part from fixing the tube end in the tubesheet, for the first identified tube, in order to verify the correctness of the tube identification; and accepting the obtained signal pattern data if the correctness of the tube identification has been verified by the comparison.

The unique signal pattern may be a unique eddy current pattern resulting, at least in part, from fixing the tube end in the tubesheet. The step of obtaining signal pattern data may include the steps of: inserting an eddy current probe into the first identified tube; and obtaining eddy current data at an elevation proximate the first identified tube.

The verification process may occur in real time by verifying the correct identification of the first identified tube while the eddy current sensor is inserted in the first identified tube. The method may include the step of: updating the baseline of eddy current patterns based upon the eddy current data obtained proximate the tube, tubesheet interface, after verifying the correct identification of the tube.

The steps of the foregoing method may be performed automatically by a computer program product structured to instruct a computer system to perform each step of the method.

As another aspect of the invention, a method of verifying the identity of an individual heat exchanger tube for inspection of a steam generator for a nuclear power generation station is provided. The steam generator includes a plurality of tubes having ends fixed in a tubesheet. The method comprises: establishing a baseline for each tube of its location in the tubesheet and its unique signal pattern resulting at least in part from fixing the tube end in the tubesheet; providing a robotic arm coupled to a portion of the steam generator and including an end-effector with a data retrieval mechanism; inserting the data retrieval mechanism into a first identified tube; obtaining signal pattern data for the first identified tube; comparing the signal pattern data obtained for the first identified tube with the baseline signal pattern resulting at least in part from fixing the tube end in the tubesheet for the first identified tube, in order to verify the correctness of the tube identification; and accepting the obtained signal pattern data if the correctness of the tube identification has been verified by the comparison.

The unique signal pattern may be the unique eddy current pattern resulting, at least in part, from fixing the tube end in the tubesheet. The data retrieval mechanism may include an eddy current probe on the end-effector.

The method may be carried out in real time by verifying the correct identification of the first identified tube while the eddy current probe is inserted in the first identified tube. The verification step may include comparing at least voltage and signal pattern eddy current data obtained for the first identified tube with the baseline voltage and signal pattern values for the tube. The method may include the step of updating the baseline, including the eddy current patterns, based upon the eddy current data obtained for the first identified tube, after verifying the correct identification of the tube.

As another aspect of the invention, a computer program product includes a computer readable medium which, when implemented by a computer system having a programmable processor, a memory storage device and an output device, instructs the computer system to execute a process for inspecting a heat exchanger having a plurality of tubes with ends fixed in a tubesheet. The process comprises the steps of: establishing a baseline for each tube of its location in the tubesheet and its unique signal pattern resulting at least in part from fixing the tube end in the tubesheet; recording the baseline for each tube in a hard drive containing a database management software, as the memory storage device; identifying a first tube; inserting a data retrieval mechanism into the first identified tube; obtaining signal pattern data for the first identified tube; comparing the signal pattern data obtained for the first identified tube with the baseline data for the tube, which is stored in the hard drive database, in order to verify the correctness of the tube identification; accepting the obtained signal pattern data if the correctness of the tube identification has been verified by the comparison or identifying another tube for comparison if the tube identification has not been verified by the comparison; updating the baseline data in the database based upon the signal pattern data obtained proximate the tube, tubesheet interface, for the identified tube, after verifying the correct identification of the tube; and performing an operation on the identified and verified tube.

The unique signal pattern may be a unique eddy current pattern resulting, at least in part, from fixing the tube end in the tubesheet. The data retrieval mechanism may be an eddy current probe. The operation performed on the verified tube may include, for example, inspecting, repairing or plugging the tube.

BRIEF DESCRIPTION OF THE DRAWINGS

A full understanding of the invention can be gained from the following description of the preferred embodiments when read in conjunction with the accompanying drawings in which:

FIG. 6 is a computer screen view of the main menu of an existing computer program product implementing a tubesheet (TS) fingerprinting tab for initiating the process of verifying the identity of a heat exchanger tube in accordance with an embodiment of the present invention.

DESCRIPTION OF THE PREFERRED EMBODIMENT

The invention will be described as applied to U-shaped heat exchanger tubes of a steam generator for a nuclear power generation system, although it will become apparent that it could also be applied to the identification, inspection and repair or servicing of other types of heat exchangers and other applications in which a plurality of generally tubular members are fixed in a transverse plate-like member, such as the exemplary tubesheet.

It will also be appreciated that while the present invention is described herein with respect to unique tube, tubesheet interface, eddy current patterns and the recording and subsequent referencing of the same, that any suitable alternative signal pattern could be used (e.g., without limitation, x-ray; thermal patterns).

As employed herein, the term "baseline" refers to a set of data for a heat exchanger tube including, for example, the tube's location in the tubesheet and its unique eddy current signal pattern or fingerprint, which results, at least in part, from the well know manufacturing process of fixing the tube end in the tubesheet. In the exemplary method, the baseline data is collected and recorded in a database for future reference and comparison, in order to verify the identity of a subsequently identified tube.

As employed herein, the term "fingerprint" refers to the unique, tube-specific eddy current signal pattern which results, at least in part, from the fixed relationship of the end of the heat transfer tube in the tubesheet.

As employed herein, the term "correctness" of the tube identification refers to how well the baseline data for an identified tube matches the corresponding newly obtained data for the identified tube. For example, the exemplary method compares matching criteria such as, voltage, phase, signal pattern or fingerprint and location in the tubesheet. If each of these matching criteria matches or is correct, within a predetermined acceptable range or deviation, the identity of the tube is verified to be correct.

Figure 1:
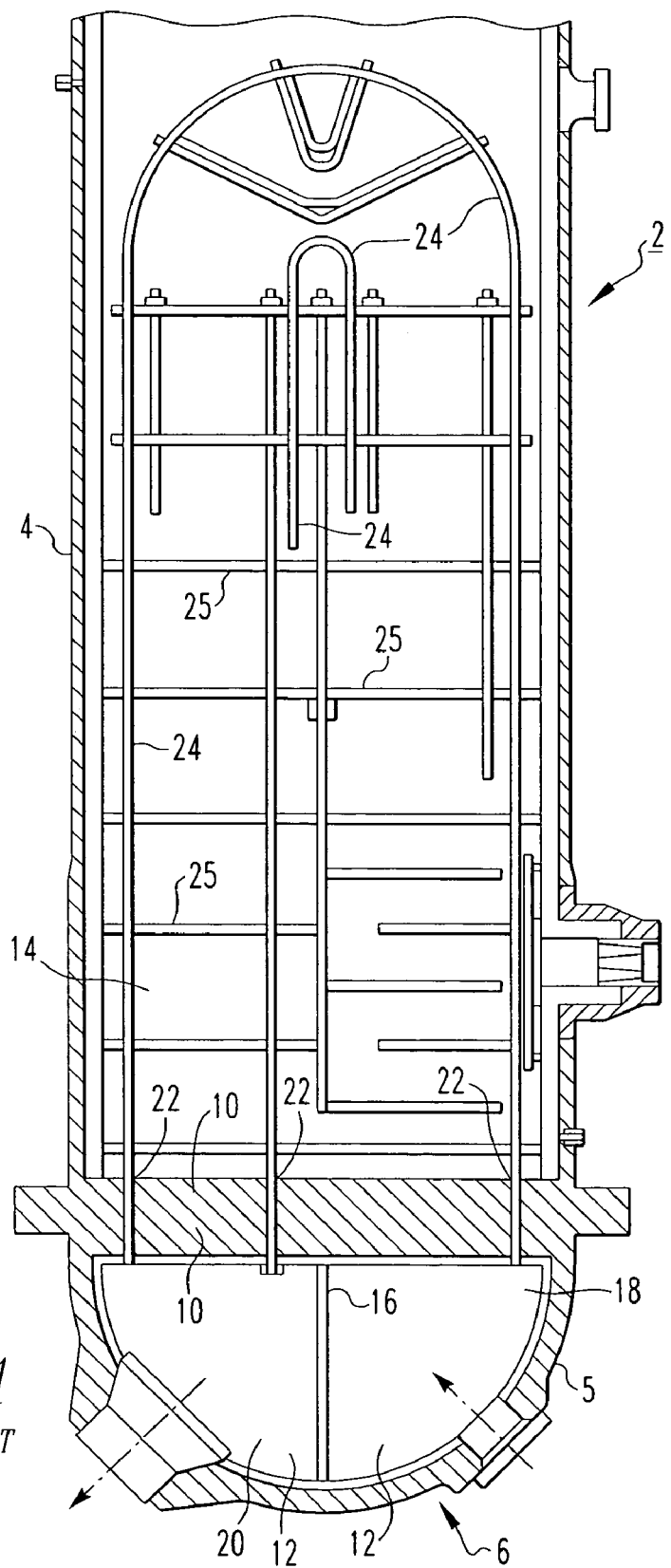
FIG. 1 is a cross-sectional view of a steam generator showing internal structures, including portions of two U-shaped heat exchanger tubes.

As shown in FIG. 1, a steam generator 2 for a nuclear power generation station (not shown) typically comprises a cylindrical pressure vessel 4 with hemispherical end sections (one hemispherical end section 6 is shown in FIG. 1). A transverse plate called a tubesheet 10 is located at the lower end of the cylindrical section 4 and divides the steam generator 2 into a primary side 12, which is the lower hemispherical section 6 below the tubesheet 10, and a secondary side 14, above the tubesheet 10. A vertical wall 16 bisects the primary side into an inlet section 18 and an outlet section 20. The tubesheet 10 is typically a thick carbon steel plate with an array of thousands of holes 22 (only three holes 22 are shown in FIG. 1, for simplicity of illustration) into which are inserted the ends of U-shaped heat exchanger tubes 24 (for ease of illustration, only portions of two U-shaped tubes 24 are shown in FIG. 1). One end of each U-shaped tube 24 is inserted into the hole 22 within the tubesheet 10 which communicates with the inlet section 18 of the primary side 12 and the other end is inserted into the hole 22 within the tubesheet 10 which communicates with the outlet section 20. The primary coolant is introduced under pressure into the inlet section 18 of the primary side 12, circulates through the U-shaped tubes 24 and exits through the outlet section 20. Water introduced into the secondary side 14 of the steam generator 2 circulates around the U-shaped tubes 24 and is transformed into steam by heat given up by the primary coolant.

As previously discussed, the tubes 24 must be inspected and/or repaired or plugged to ensure that no reactor coolant leaks into the secondary side 14 of the generator 2, which would contaminate the steam. Eddy current testing is commonly used to inspect steam generator tubes. See, e.g., U.S. Pat. Nos. 3,302,105; 3,693,075; 4,194,149; 4,207,520; 4,631,688 and 4,763,274.

For example, as disclosed in U.S. Pat. No. 4,763,274, it is well known in the field of eddy current testing that variations in the characteristics of the tubes 24 such as dents, flaws such as pitting, cracks, and thinning of the walls, as well as the presence of adjacent structures such as support plates 25 and the tubesheet 10, influence the effective impedance of the eddy current probe coils (not shown) and thus the eddy current signal pattern or fingerprint (see, for example, baseline tube signal pattern 214 in FIG. 8) for each tube 24. The present invention utilizes these unique, tube-specific eddy current tubesheet signal patterns to quickly and accurately verify the identity of individual steam generator tubes 24, thereby ensuring that the correct tube 24 is being inspected and/or serviced and that the steam generator 2 is not mistakenly returned to service with a degraded tube 24 that was not serviced or plugged due to a mis-encoding or incorrect identification of the tubes 24.

It is well known that when a steam generator 2 is manufactured, that the ends of the heat exchanger tubes 24 are typically fixed in the tubesheet 10. Thus, unique tubesheet signal patterns result, such as eddy current signal patterns, because of the fixed nature of the tube end within the tubesheet 10, which should not be effected by normal year-to-year steam generator 2 operations, the signal patterns should not change throughout the life of the steam generator 2. Therefore, as previously discussed, these unique, tube-specific eddy current signal patterns can be used as a fingerprint for each tube 24. The exemplary method of the present invention provides a method of establishing a baseline of these fingerprints and other tube data, expressly including, but not limited to, the tube 24 position on the tubesheet 10 (i.e., a cartograph database of each tube position recorded in x, y cartesian coordinates). When it is subsequently desired to perform an operation such as inspection or repair, on an identified tube 24, this baseline data is compared to newly obtained eddy current data for the identified tube 24, in order to verify the identity of the tube. It will be appreciated that the eddy current data may be acquired using any known or suitable method of eddy current data collection expressly including, but not limited to, such methods disclosed in previously-referenced U.S. Pat. Nos. 3,302,105; 3,693,075; 4,194,149; 4,207,520; 4,631,688 and 4,763,274. For example, an eddy current probe (shown generically as reference 36 in FIGS. 2 and 4) can be inserted into the identified tube 24, in order to collect eddy current data. The foregoing patents discuss variations in the method of collecting such data extensively. The exact method or process and apparatus used to obtain the eddy current data are not meant to be a limiting aspect of the present invention.

Accordingly, the method of the present invention provides an easy, yet accurate method of tube verification without requiring, for example, physical modification of the tube (see, e.g., U.S. Pat. No. 5,321,887 disclosing the embossing of impressions in the form of a bar code on the interior or exterior of the tubes) and while avoiding the aforementioned tube identification problems plaguing the known prior art methods of tube identification and inspection (e.g., operator or analyst human-error; image capturing technology difficulties; software communication breakdowns; calibration difficulties).

Figure 4:
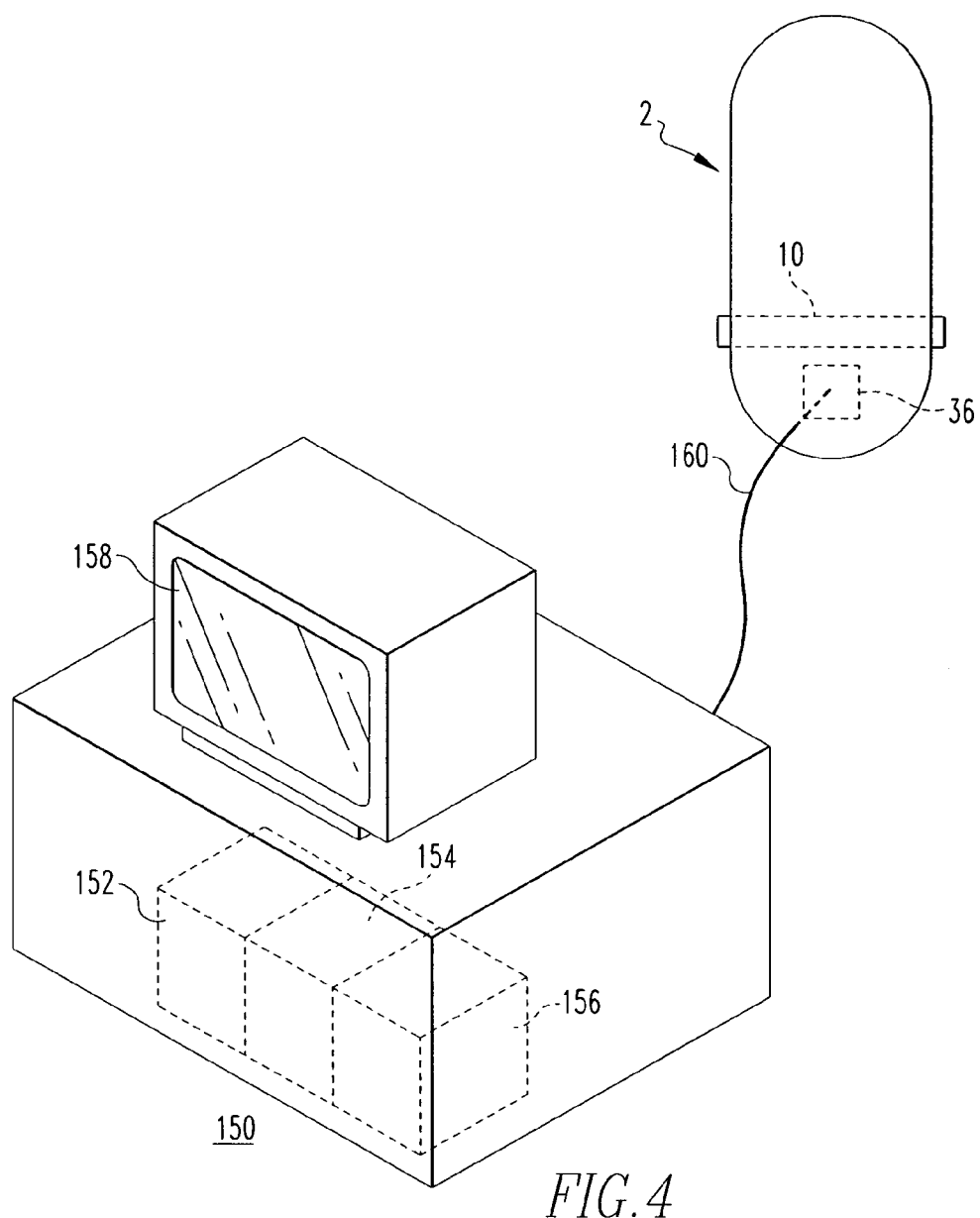
FIG. 4 is an isometric, schematic view of a computer system for performing the method of inspecting a heat exchanger of FIG. 3.

The exemplary method is also easy and relatively inexpensive to implement. For example, implementing the method involves the relatively simple process of creating the previously discussed baseline for each tube 24 in the tubesheet 10. The baseline data may be collected for example, during an initial inspection following the construction of the steam generator 2, or in the case of an existing, operating steam generator 2, the baseline data may be collected during a standard inspection outage or downtime. The baseline fingerprint signal pattern for each tube 24 is preferably selected by an analyst. In the exemplary method, the baseline fingerprint signal patterns are stored in a computer database 154 (FIG. 4). The exemplary method is thus much easier and less expensive to implement than, for example, the method disclosed in U.S. Pat. No. 5,321,887, which requires physical modification of every tube.

Figure 2:
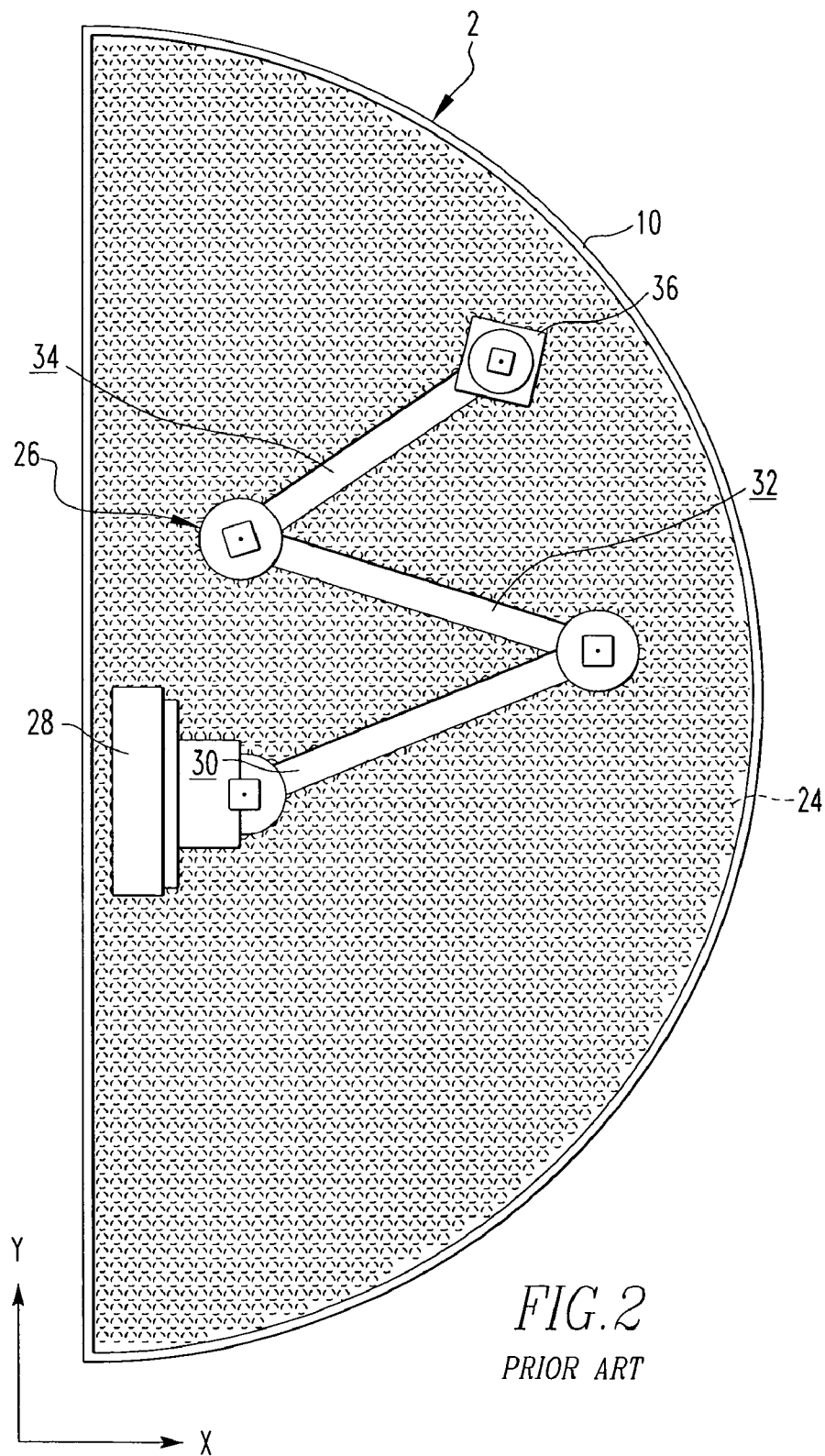
FIG. 2 is a bottom plan view of the underside of a tubesheet of an inlet section of the steam generator of FIG. 1 and a robotic arm disposed on the underside of the tubesheet, with the ends of the plurality of U-shaped tubes, which are fixed in the tubesheet, shown in phantom line drawing.

A still further advantage of the method of inspecting steam generator tubes 24 of the present invention is that it may be implemented with existing tube inspection and identification systems to complement and improve the existing system. For example, FIG. 2 illustrates an existing tube identification and servicing system with which the present invention may be implemented. In this example, a robotic arm, shown in generic form and indicated generally as reference 26, is located beneath the tubesheet 10 of the steam generator 2 (a partial and schematic view of the tubesheet 10 is shown in FIG. 2). As shown, the ends of thousands of tubes 24 (shown in phantom line drawing) are disposed in the tubesheet 10. The robotic arm 26 includes a base 28 that is secured to a structural member (not shown). A number of articulating links 30, 32 and 34 permit the robotic arm 26 to move across the tubesheet 10 to a first identified tube 24. A suitable actuator (not shown), such as, for example, a stepping motor, drives the robotic arm 26 to the desired position. Accordingly, the robotic arm 26 can be controlled to access the tubes 24 for inspection, service or repair thereof. An end-effector 36 including a data retrieval mechanism, such as the exemplary eddy current inspection probe 36, is mounted to the end of the robotic arm 26. For example, in FIG. 2, the end-effector 36 is mounted to the end of link 34 of the robotic arm 26 for eddy current inspection of an identified tube 24.

It will be appreciated that the end-effector could include such tools and items as, for example, a guide pin (not shown), a tube-end alignment clamp (not shown), various types of tooling (not shown), and a television camera that outputs a video signal to a remotely located system operator, in addition to the exemplary eddy current inspection probe 36. End-effectors are well known in the art. See, e.g., U.S. Pat. No. 5,878,151 (discussing various types of end-effector tooling).

FIG. 2 is representative of the robotic arm 26 employed in the independent tube position verification system disclosed in U.S. Pat. No. 6,282,461. As disclosed therein, in operation, the robotic arm 26 can be moved by appropriate commands from an operated-control joystick or by entering target x, y coordinates into a controller (not shown) that causes the robotic arm 26 to move to the target tube 24. The verification system disclosed in U.S. Pat. No. 6,282,461 employs an end-effector 36 including a television camera (not shown) and lighting sources (not shown) to capture successive image frames, in order to collect displacement information with respect to a reference artifact, such as a plugged tube (not shown), in the image field. The displacement information is then converted into velocity and direction information, which is compared against position information maintained by the robotic arm 26. However, as previously discussed, both the image capturing system (not shown) and the robotic arm 26 suffer from calibration and operational problems that affect the accuracy of the tube 24 identification and verification. For example, the robotic arm 26 may be subject to bending forces (i.e., in the z direction (not shown in FIG. 2); the z plane is perpendicular to the x-y plane of the tubesheet 10), particularly when the robotic arm 26 is fully extended with respect to its base 28. Unintended bending deflection of the robotic arm 26 can result in the end-effector 36 being positioned over a tube 24 that is different from the intended target.

Additionally, the image capturing system, which is designed to compare tube position information with that of the robotic arm 26 is also susceptible to errors. For example, accuracy of the image capturing data relies upon reference to a readably recognizable reference in the image field, such as, for example, a plugged tube (not shown) or the edge of the tubesheet 10. However, as large areas of the tubesheet 10 may not contain such a distinguishable reference, calibration errors may occur. Furthermore, distortion and other image capturing difficulties, caused for example by lighting (i.e., shadows and glare) or by the position of the television camera (not shown) or the speed at which the end-effector 36 on which it is disposed, is traveling, can result in mis-encoding or improper identification of a tube 24.

Figure 3:
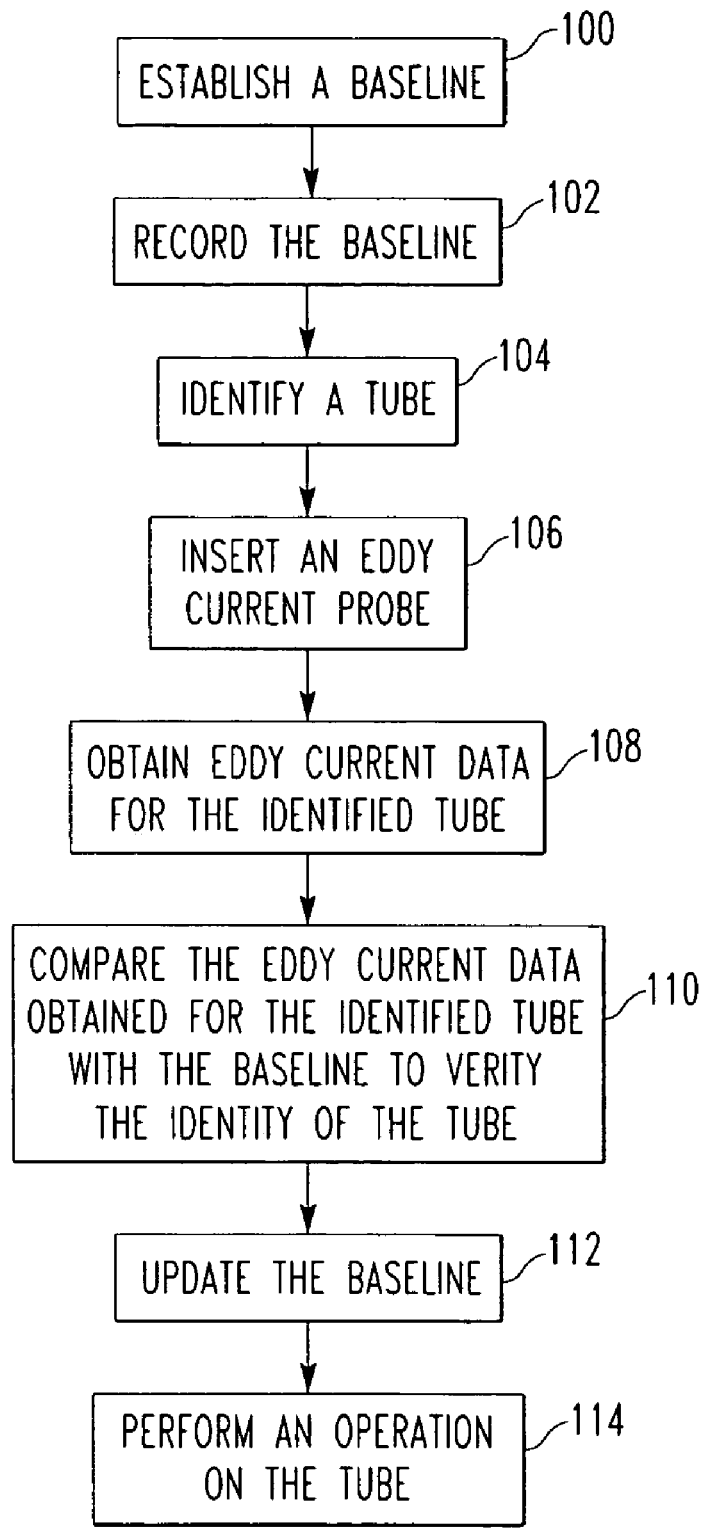
FIG. 3 is a flow diagram of a method of inspecting a heat exchanger in accordance with the present invention.

Hence, the method of the present invention may be implemented to supplement and compliment the foregoing representative system, in order to overcome the deficiencies thereof. FIG. 3 shows a flow diagram of the exemplary method. As shown, the method comprises a first step 100 of establishing a baseline for each tube 24. As previously discussed, the exemplary baseline includes the tube's 24 location on the tubesheet 10 and tube-specific unique eddy current data including the tube's fingerprint (see, for example, baseline tube signal pattern 214 and newly obtained signal pattern 216 in FIG. 7).

The next step 102 of the exemplary method is to record the baseline data for each tube 24. The exemplary method is computerized, employing a computer system 150 (FIG. 4) having a programmable processor 152 (FIG. 4), a memory storage device, such as the exemplary hard drive containing a database management software 154 (FIG. 4), a computer program product 156 (FIG. 4) and an output display, such as the exemplary computer screen 158. Accordingly, the exemplary baseline is recorded in the hard drive 154. The next step 104 is to identify a first tube 24 to be inspected and/or serviced. Next, in step 106, an eddy current probe 36 (FIG. 2) is then inserted into the first identified tube 24. It will be appreciated that this step 106 and the next step 108 of obtaining eddy current data from the first identified tube 24, may be accomplished in accordance with any of the well known methods of eddy current testing or any suitable alternative method discussed in the above-referenced patents. For example, the end-effector 36 (FIG. 2) and robotic arm 26 (FIG. 2), previously discussed in connection with FIG. 2, and disclosed in detail in U.S. Pat. No. 6,282,461, may be employed to facilitate these steps 106, 108, respectively. In step 110, the newly obtained eddy current data retrieved from the first identified tube 24 is then compared to the baseline eddy current data, in order to verify the identity of the tube 24.

Once the identity of the tube 24 is verified, the exemplary process includes step 112, updating the fingerprint baseline data. Specifically, in the event any changes have occurred with respect to the fingerprint of the tube 24, the method of the present invention will update the exemplary hard drive database 154 to reflect the changes so that the fingerprint data is current for future reference when subsequent identity verification, inspection and/or servicing of the same tube 24 is desired. The final step 114 of the exemplary method is to proceed with performing an operation on the tube 24. Step 114 may involve performing such operations on the tube 24 as, for example, inspecting the tube 24, repairing the tube 24 or plugging the tube 24.

While the present invention has been discussed herein as supplementing an existing inspection system (FIG. 2), it will be appreciated that it can be used with any robotic arm system or manual process to identify or confirm the location of each tube of the heat exchanger.

As previously discussed, the exemplary method is preferably computerized. FIG. 4 illustrates a schematic representation of the computer system 150, which includes the programmable processor 152, the memory storage device 154, the computer program product 156 and the output display. The exemplary memory storage device includes the hard drive containing database management software for recording the 154 baseline tube data. The exemplary output display device is a computer screen 158, as shown. The computer program product 156 includes computer readable medium which, when implemented by the computer system 150 instructs the programmable processor 152 to carry out the steps of the exemplary method shown in FIG. 3. As shown, the exemplary computer system 150 is electrically connected to the eddy current probe end effector (shown generically as reference 36) by computer cables 160. However, it will be appreciated that the computer system 150 could alternatively communicate with the eddy current probe 36 using any alternative known or suitable communication mechanism (not shown), such as, an optical port (i.e., input; output) or a wireless port (i.e., radio frequency; infrared; input; output).

Continuing to refer to FIG. 4, the computer program product (shown generically as reference 156) collects the eddy current data from the identified tube 24 (not shown in FIG. 4) and performs the comparison between the newly obtained data and the baseline to determine whether or not the matching criteria, for example, voltage, phase, signal pattern and tubesheet location, sufficiently match. If the similarity between the eddy current data newly obtained for the first identified tube 24 (FIG. 2) and the baseline data stored in the database is not within the predetermined acceptable range, the exemplary computer program product 156 will instruct the computer system 150 to alert the analyst or operator of possible incorrect identification or mis-encoding of the tube 24. The exemplary alert is a visual prompt or message on the computer screen 158. Alternatively, if the obtained eddy current data sufficiently matches the baseline data, the computer program product 156 will instruct the computer system 150 to indicate that the correctness of the tube identification has been verified by displaying, for example, a "PASS" (see, for example, the eddy current results computer screen 204 of FIG. 6) or similar suitable message or prompt on the computer screen 158. The matching criteria and the determination of whether or not the matching criteria sufficiently match can be programmed by the analyst. For example, the analyst may specify an acceptable range of deviation between the newly obtained data and the baseline data, within which the identity of the tube 24 will be verified. In this manner, the analyst may determine what data to compare and how closely the compared data must match.

Unlike known prior art tube verification systems, such as the image capturing tube verification system, previously discussed in connection with FIG. 2, which has a delay as captured images and associated displacement information are processed and compared with the robotic arm 26 calculations, the method and computer program product 156 of the present invention permits tube verification and inspection or servicing to occur instantaneously, in real time. Specifically, eddy current data can be collected and compared to the baseline data in the database 154 while the eddy current probe 36 is within the tube 24, thereby providing instantaneous verification of the identity of the first identified tube 24, prior to moving the probe 36 or end-effector to the next tube 24. It will be appreciated that the exemplary computer program product 156 may also permit an analyst to program the programmable processor 152 to perform the steps of the exemplary method (FIG. 3) in an automatic mode. For example, the processor 152 could be programmed to flag (i.e., send a user prompt or message to the computer screen 158) potentially incorrectly identified tubes 24 while proceeding with the inspection and/or service of correctly identified and verified tubes 24. The status of each tube 24 may then be outputted to the computer screen 158 (see for example, computer screens 200, 204 and 212 in FIGS. 6, 7 and 8 respectively) for the analyst or operator to view and interpret.

Figure 5:
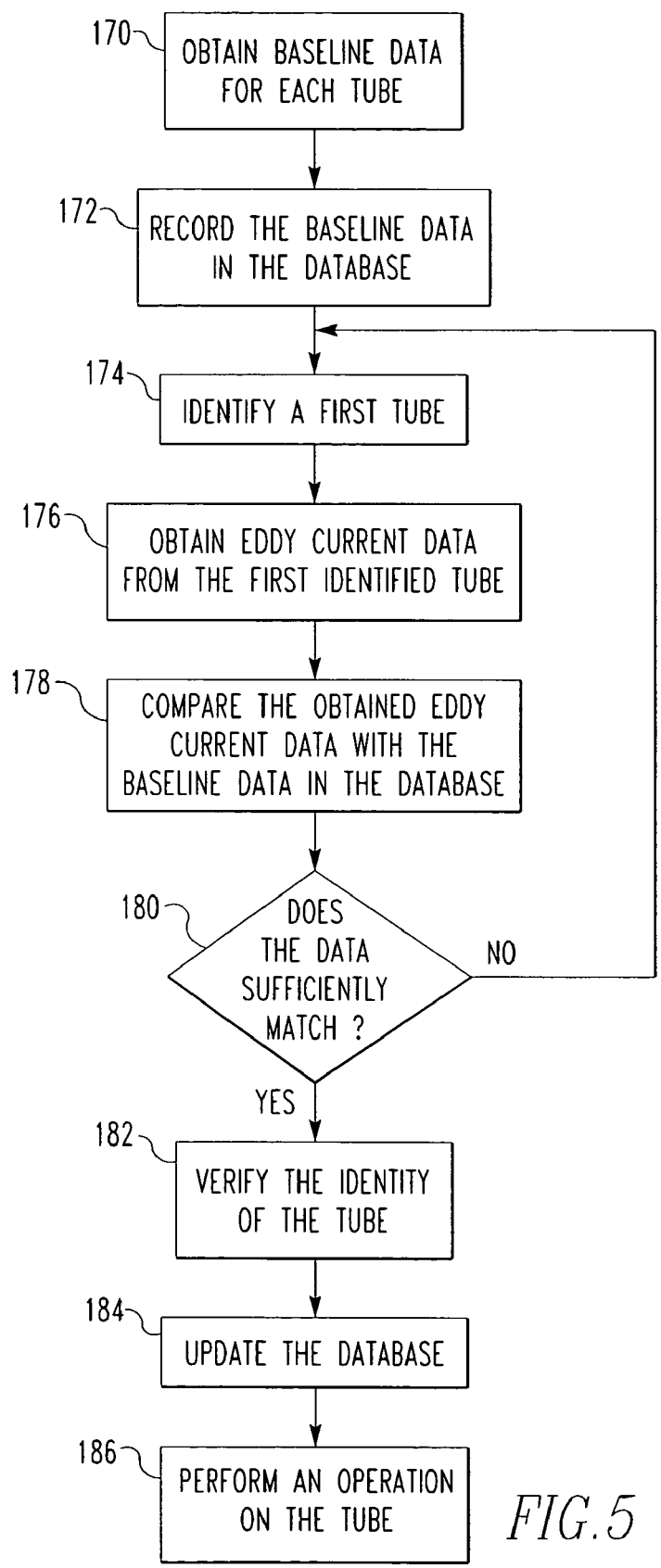
FIG. 5 is a flow diagram of a computer program product for instructing the computer system of FIG. 4 to perform the method of FIG. 3, in accordance with an embodiment of the present invention.

FIG. 5 shows a flow diagram of the exemplary computer program product 156 (FIG. 4). As shown, the computer program product 156 (FIG. 4) essentially instructs the computer system 150 (FIG. 4) to carry out the method shown in FIG. 3 for inspecting a heat exchanger.

The first step 170 is to obtain baseline data for each tube in the tubesheet 10 (FIGS. 1 and 2). As previously discussed, the baseline data preferably includes the tube's 24 location in the tubesheet 10 and its unique eddy current pattern resulting, at least in part, from fixing the tube end in the tubesheet 10. The baseline data may be obtained using any of the aforementioned methods of collecting eddy current data. See, e.g., above-referenced U.S. Pat. No. 4,763,274. Next, in step 172, the baseline data is then recorded in the exemplary hard drive 154.

To begin the process of, for example, inspecting a tube 24 or tubes 24 of the steam generator 2, the exemplary computer program product 156 (FIG. 4) instructs the programmable processor 152 (FIG. 4) of the computer system 150 (FIG. 4) to perform the step 174 of identifying a first tube 24. In the next step 176, eddy current data is obtained for the first identified tube 24. This step 176 may be performed, for example, by the programmable processor 152 (FIG. 4) instructing the robotic arm 26 (FIG. 2) to move so as to permit the exemplary eddy current probe end-effector 36 (FIGS. 2 and 4) to be inserted into the first identified tube 24 for retrieving eddy current data therefrom. The computer program product 156 (FIG. 4) then instructs the computer system 150 to perform step 178 of comparing the obtained eddy current data with the baseline data in the hard drive database 154. The next step 180 is to determine whether or not the compared data sufficiently matches. As shown, if the data does not sufficiently match within the aforementioned user-specified predetermined range of acceptability, another tube 24 will be identified and the verification process will start over. If, however, the compared data does sufficiently match, the process proceeds to the next step 182 of verifying the identity of the tube. Once the identity of the tube 24 has been verified, the hard drive database 154 may be updated based upon the obtained eddy current data for the first identified tube 24. Next, in step 186, the desired operation may then be performed on the tube 24. For example, following step 182 of verifying the identity of the tube 24, inspection, repair or plugging of the tube 24 may proceed.

Figure 6:
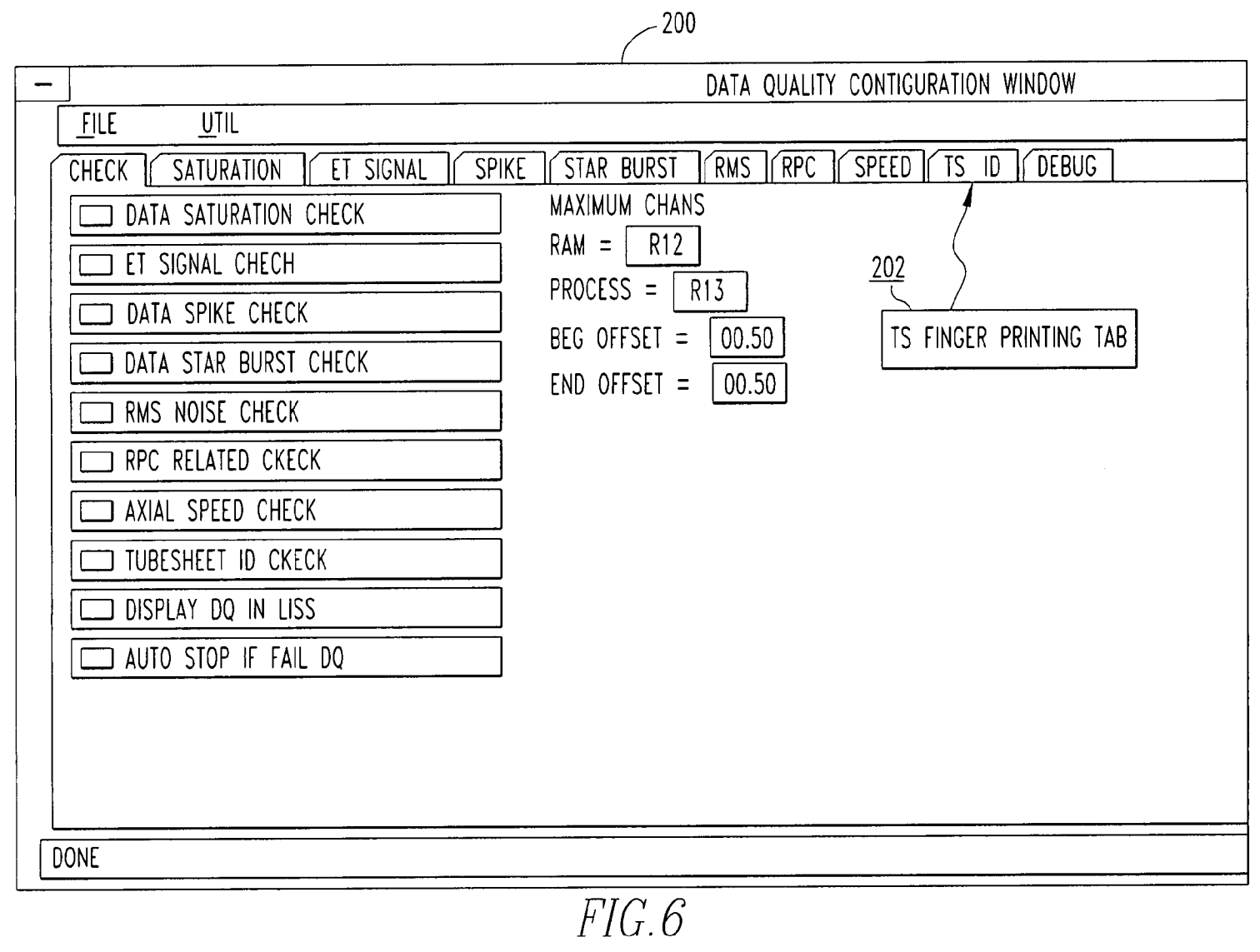
Figure 7:
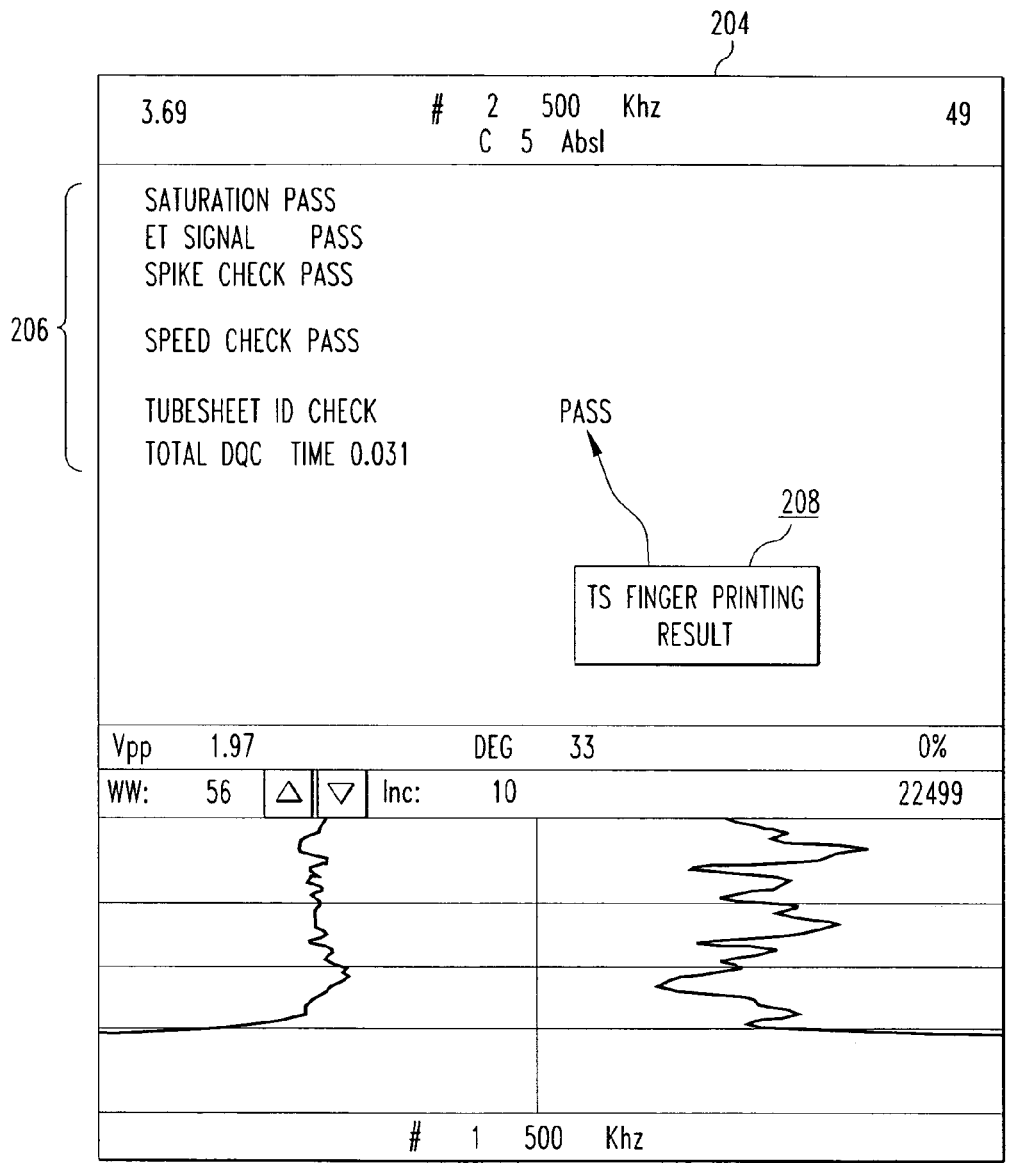
FIG. 7 is a computer screen view showing the results of a tube verification process being run in real time, in accordance with an embodiment of the present invention.
Figure 8:
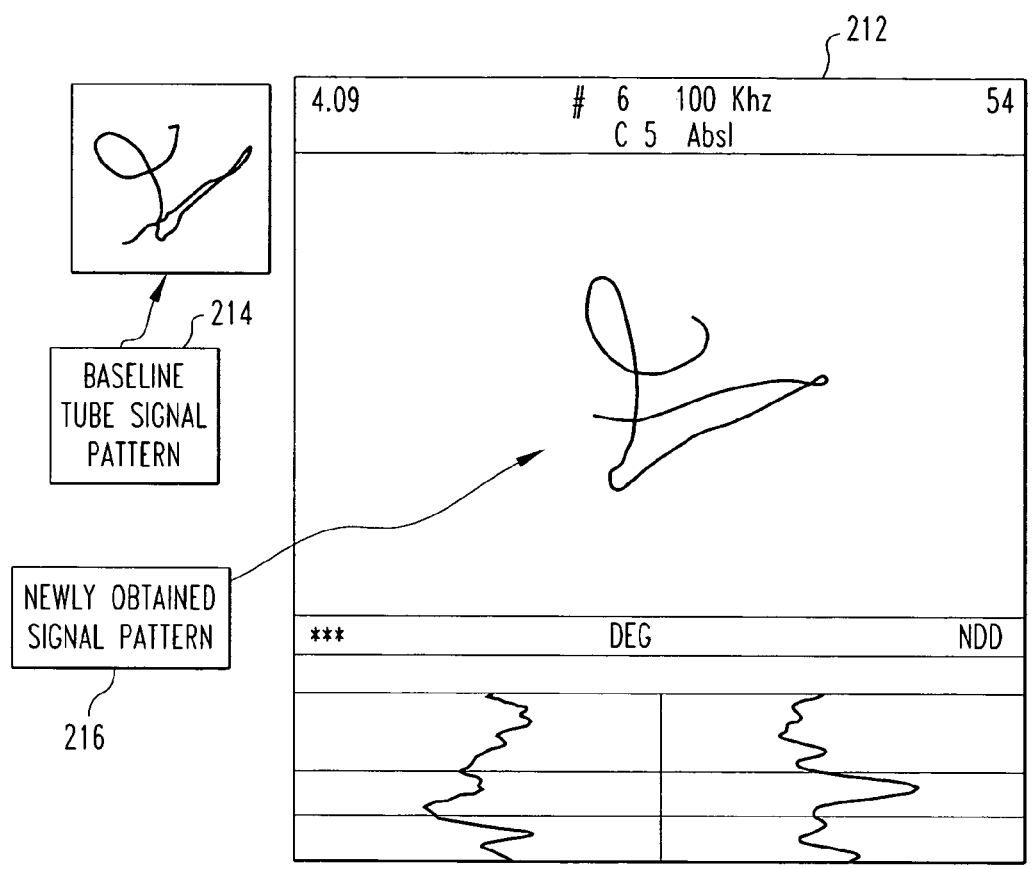
FIG. 8 is computer screen view showing the baseline eddy current signal pattern for a tube being compared to the newly obtained signal pattern for the tube, in accordance with an embodiment of the present invention.

Referring now to FIGS. 6–8, as previously discussed, the exemplary method may be used to compliment an existing data collection and quality control computer system and computer program product. For example, the Assignee hereof currently employs a Data Quality Monitoring (DQM) computer program product for use in, for example, collecting and checking the accuracy of the steam generator 2 data. DQM is licensable from Westinghouse Electric Company, LLC, Waltz Mill, Madison, Pa. 15663. FIGS. 6–8 show several computer screen snap-shot views representative of how the method of the present invention can be implemented, for example, with the existing DQM data collection system.

FIG. 6 is a snap-shot illustration of the DQM computer program main menu window 200. The main menu has a number of selection tabs corresponding to a number of different data selection options, such as, for example, the exemplary tubesheet (TS) fingerprinting tab 202, shown. Selecting the exemplary TS fingerprinting tab 202 enables the analyst or operator to perform a tube 24 verification in accordance with the method of the present invention (best shown in FIG. 3). For example, as previously discussed, the analyst or operator may establish a predetermined acceptable range or deviation in the matching criteria (i.e., voltage; phase; signal pattern; tubesheet position) between the baseline values and the eddy current data being obtained for the identified tube 24. Whether or not the results of the comparison of the matching criteria fall within this user-specified deviation or range of acceptability determines whether or not the identity of the tube 24 will be verified and thus whether the desired operation should be performed on the tube 24. The results of the computerized comparative analysis are shown, for example, on a results screen (see, for example, FIGS. 6 and 7).

FIG. 7 illustrates the results of an example of the exemplary verification process, as displayed on an eddy current results computer screen 204. As shown, the results screen 204 optionally includes a short summary of data quality results 206 with respect to the acceptability (i.e., indicated by a "PASS" prompt or message) or unacceptability (not shown) regarding the correctness of eddy current data parameters (saturation, signal, spike, speed and tube identification parameters are shown in FIG. 7). As previously discussed, acceptability of the parameters (as indicated by the "PASS" messages in FIG. 7), relies upon the predetermined acceptable deviations or ranges of such values, which can be established or programmed by the analyst or operator. As shown, the exemplary results screen 204 also displays the actual tube verification or TS fingerprinting result 208. The identified tube 24 in FIG. 7 passed, thus indicating that the identity of the tube 24 was verified. Additionally, as previously discussed, the method of the present invention enables the operator to view the results in real time, at acquisition. As such, the results screen 204 may optionally further include a real time graphical representation 210 of the eddy current data being retrieved from the tube 24, as shown.

FIG. 8 illustrates a fingerprint signal pattern display screen 212. As shown, the baseline eddy current signal pattern or fingerprint 214 for the identified tube 24 is accessed and retrieved from the database 154 for comparative display proximate the newly obtained fingerprint or signal pattern 216. In the exemplary embodiment, the baseline tube signal pattern 214 and newly obtained tube signal pattern 216 are visually displayed adjacent one another on the same results screen 212, in order that the operator or analyst may make a quick and accurate visual comparison of the two fingerprint patterns and thereby visually confirm the tube identity verification or TS fingerprinting result 208 (FIG. 7).

Accordingly, the present invention provides a fast and accurate method of verifying the identity of steam generation tubes 24 by establishing a database 154 of unchanging, tube-specific eddy current baseline data and employing a comparative computer program product 156 for instructing a computer system 150 to, among other things, access the database 154 and compare it with newly obtained data collected for the tube 24. The invention also overcomes the longstanding calibration and mis-encoding disadvantages of the known prior art without requiring, for example, physical modification of the tube 24. Tube identification encoding errors caused, for example, by human error and communication breakdowns between the robot and/or the visual tube position verification system and data collection software are also avoided. Therefore, the present invention provides a low cost solution for complying with new and increasingly stringent Electrical Power Research Institute (EPRI) inspection guideline data quality requirements for verifying and ensuring eddy current probe 36 delivery to the correct tube 24, while having minimal impact on steam generator 2 operations.

It will be appreciated that the Figures provided herein are only intended to illustrate the principle behind the described embodiments of the invention. For example, it will be appreciated that the method of the present invention could be employed in conjunction with any known or suitable computer program product or computer system other than those described herein. Moreover, any variety of tube data parameters other than, or in addition to, the exemplary voltage, phase and signal pattern could be used to identify and verify the identity of the tubes 24. It will also be appreciated that the computer system 150 and computer program product 156 could be utilized to convey the results of the aforementioned tube identity verification process to the analyst or operator, in any suitable manner other than the exemplary computer screen 158 output displays (references 200, 204 and 212) illustrated in FIGS. 6–8 and discussed herein. For example, the results could be outputted on a printed hardcopy page (not shown).

Therefore, while specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. A method of inspecting a heat exchanger comprising a plurality of tubes having ends fixed in a tubesheet, comprising the steps of:
    establishing a baseline for each tube of its location in the tubesheet and its unique signal pattern resulting at least in part from fixing the tube end in the tubesheet;
    obtaining signal pattern data at an elevation proximate a first identified tube;
    comparing the signal pattern data obtained for the first identified tube with the baseline signal pattern resulting at least in part from fixing the tube end in the tubesheet for the first identified tube, in order to verify the correctness of the tube identification; and
    accepting the obtained signal pattern data if the correctness of the tube identification has been verified by the comparison.

2. The method of claim 1 wherein the signal pattern is an eddy current pattern resulting at least in part from fixing the tube end in the tubesheet; and wherein the step of obtaining signal pattern data includes the steps of:
    inserting an eddy current probe into a first identified tube; and
    obtaining eddy current data at an elevation proximate the first identified tube.

3. The method of claim 2, including the step of:
    verifying the correct identification of the first identified tube while the eddy current probe is inserted in the first identified tube.

4. The method of claim 2 including the step of:
    updating the baseline of eddy current patterns based upon the eddy current data obtained proximate the tube, tubesheet interface, after verifying the correct identification of the tube.

5. The method of claim 2 wherein said step of establishing a baseline includes the step of obtaining eddy current data for each tube selected from the group consisting of voltage, phase and signal pattern.

6. The method of claim 5 including the steps of:
    obtaining eddy current data for the first identified tube that corresponds to the baseline data, including eddy current data selected from the group consisting of voltage, phase and signal pattern; and
    comparing at least one of the corresponding voltage, phase and signal pattern obtained for the first identified tube with the corresponding baseline data.

7. The method of claim 1 wherein the steps of claim 1 are performed automatically a computer program product.

8. The method of claim 1 including the step of performing an operation on the identified, verified tube selected from the group consisting of inspecting the tube, repairing the tube or plugging the tube.

9. The method of claim 1 wherein the heat exchanger is a steam generator for a nuclear power generation station.

10. A method of verifying the identity of an individual heat exchanger tube for inspection of a steam generator for a nuclear power generation station, the steam generator including a plurality of tubes having ends fixed in a tubesheet, the method comprising:
    establishing a baseline for each tube of its location in the tubesheet and its signal pattern resulting at least in part from fixing the tube end in the tubesheet;
    providing a robotic arm coupled to a portion of the steam generator, the robotic arm including an end-effector with a data retrieval mechanism;
    inserting the data retrieval mechanism into a first identified tube;
    obtaining signal pattern data at an elevation proximate the first identified tube;
    comparing the signal pattern data obtained for the first identified tube with the baseline signal pattern resulting at least in part from fixing the tube end in the tubesheet for the first identified tube, in order to verify the correctness of the tube identification; and
    accepting the obtained signal pattern data if the correctness of the tube identification has been verified by the comparison.

11. The method of claim 10 wherein the unique signal pattern is a unique eddy current pattern resulting at least in part from fixing the tube end in the tubesheet; wherein the data retrieval mechanism is an eddy current probe; and wherein the step of obtaining signal pattern data includes the steps of:
    inserting the eddy current probe into the first identified tube; and
    obtaining eddy current data at an elevation proximate the first identified tube.

12. The method of claim 11, including the step of:
    verifying the correct identification of the first identified tube while the eddy current probe is inserted in the first identified tube.

13. The method of claim 11 wherein the verification includes:
    comparing at least voltage and signal pattern eddy current data obtained for the first identified tube with the baseline voltage and signal pattern values for said tube.

14. The method of claim 11 including the step of:
updating the baseline, including the eddy current patterns, based upon the eddy current data obtained proximate the tube, tubesheet interface, for the first identified tube, after verifying the correct identification of said tube.

15. A computer program product which, when implemented by a computer system having a programmable processor, a memory storage device and an output device, instructs the programmable processor of said computer system to execute a process for inspecting a heat exchanger having a plurality of tubes with ends fixed in a tubesheet, the process comprising the steps of:
establishing a baseline for each tube of its location in the tubesheet and its unique signal pattern resulting at least in part from fixing the tube end in the tubesheet;
recording the baseline for each tube in a database within the memory storage device of said computer system;
identifying a first tube;
inserting a data retrieval mechanism into the first identified tube;
obtaining signal pattern data at an elevation proximate the first identified tube;
comparing the signal pattern data obtained for the first identified tube with the baseline data for said tube, which is stored in the database, in order to verify the correctness of the tube identification;
accepting the obtained signal pattern data if the correctness of the tube identification has been verified by the comparison or identifying another tube for comparison if the tube identification has not been verified by the comparison;
updating the baseline data in the database based upon the signal pattern data obtained at the tube, tubesheet interface, for the identified tube after verifying the correct identification of said tube; and
performing an operation on the identified and verified tube.

16. The computer program product of claim 15 wherein the unique signal pattern is an eddy current pattern rebutting at least in part from fixing the tube end in the tubesheet; wherein the data retrieval mechanism is an eddy current probe; and wherein the step of obtaining signal pattern data includes the steps of:
inserting the eddy current probe into the first identified tube; and
obtaining eddy current data at an elevation proximate the first identified tube.

17. The computer program product of claim 16 wherein the step of verifying the correct identification of the first identified tube occurs while the eddy current probe is inserted in the first identified tube.

18. The computer program product of claim 16 wherein the verification step includes comparing at least voltage and signal pattern eddy current data obtained for the first identified tube with the baseline voltage and signal pattern eddy current data stored in the database for said tube.

19. The computer program product of claim 16 wherein said output device of said computer system includes at least one computer screen; and wherein the results of the comparison between the eddy current data obtained for the first identified tube and the baseline eddy current data stored in the database for said tube, are displayed on said at least one computer screen.

20. The computer program product of claim 15 wherein said operation performed on the verified tube includes an operation selected from the group consisting of inspecting, repairing and plugging.

* * * * *